United States Patent [19]

Tomoff et al.

[11] 4,176,956
[45] Dec. 4, 1979

[54] SAMPLE TUBE MOUNTING STRUCTURE FOR FLAMELESS ATOMIC ABSORPTION SPECTROSCOPY

[75] Inventors: Toma Tomoff, Überlingen; Rolf G. A. Tamm, Salem, both of Fed. Rep. of Germany

[73] Assignee: Bodenseewerk Perkin-Elmer & Co. GmbH, Überlingen, Fed. Rep. of Germany

[21] Appl. No.: 890,730

[22] Filed: Mar. 27, 1978

[51] Int. Cl.² ............................................. G01J 3/30
[52] U.S. Cl. .................................. 356/312; 356/244
[58] Field of Search ......................... 356/85, 244, 312

[56] References Cited

U.S. PATENT DOCUMENTS

| 4,019,372 | 4/1977 | Parkell et al. ........................ 356/181 |
| 4,022,530 | 5/1977 | Braun et al. .......................... 356/244 |

FOREIGN PATENT DOCUMENTS 2501507 7/1976 Fed. Rep. of Germany ............. 356/85

*Primary Examiner*—Vincent P. McGraw
*Attorney, Agent, or Firm*—Salvatore A. Giaratana; Francis L. Masselle; Edwin T. Grimes

[57] ABSTRACT

The graphite sample tube used in flameless atomic spectroscopy is mounted in coaxial bores of two separated heating electrodes, each supported by a cooling jacket for carrying off the excess heat produced by the sample tube. Instead of being sealed with sealing rings, the cooling jackets contain seamless tubing that is tightly pressed in the grooves and carries a flow of suitable coolant. The tubing eliminates fluid eddies and thermal stresses which inevitably leads to coolant leaks. An additional feature is that one of the two cooling jacket housings is pivotally movable by a pneumatic actuator for easy removal of the graphite sample tubes and the inspection of the bores of the electrodes.

11 Claims, 3 Drawing Figures

SAMPLE TUBE MOUNTING STRUCTURE FOR FLAMELESS ATOMIC ABSORPTION SPECTROSCOPY

CROSS-REFERENCE TO RELATED APPLICATION

The invention described and claimed herein is closely related to copending patent application Ser. No. 787,036, filed Apr. 13, 1977, and assigned to the assignee of the present invention. The copending application describes a similar type of support structure for a graphite sample tube and includes a pair of cooling jacket assemblies, each of which supports an electrode having coaxial annular bores in which the graphite sample tube is supported. The cooling jacket housing portions are selectively movable either toward or away from each other axially and under the power of a drive mechanism, such as a pneumatic actuator, and cooling is effected by annular cooling chambers in the cooling jacket housing and surrounding each electrode. The cooling chambers are sealed with annular rings.

In this prior art assembly, the passages machined in the cooling jackets have presented certain problems. When used over extended periods, eddies are generated within the passages and prevent the necessary cooling of the cooling jacket assembly and electrodes. Furthermore, since the cooling jackets are being subjected to heavy thermal stresses, very fine pockets and crevices in the material will develop and will result in leaks in the passages and the corresponding development of steam or vaporized coolant.

In the operation of the prior art system described above, a graphite sample tube is removed by axially parting the cooling jacket housings and the electrodes axially mounted therein by the use of a reversible drive mechanism. While such a system was a great advance over the then existing art, it has been found that repeated removals and insertion of graphite tubes during multiple spectroscopic tests are inconvenient and, furthermore, since the bores of the electrodes are separated axially, it is not possible to inspect the bores for possible damage or contamination without an inspection mirror.

The present invention provides greatly improved cooling without the possibility of coolant leakage, and the cooling jacket housings are separable to permit easy inspection of their bores.

Briefly described, the improved cooling is obtained by providing the end surfaces of the cooling jacket housings with annular channels containing seamless tubing through which a suitable coolant is pumped, and the improved housing separation is realized by pivoting one of the housings so that the housings and their respective electrodes are separated at a steep angle relative to each other.

DESCRIPTION OF THE DRAWINGS

In the drawings which illustrate the preferred embodiment of the invention.

DETAILED DESCRIPTION OF THE PREFERRED EMBODIMENT

In flameless atomic absorption spectroscopy, a sample material to be analyzed is admitted into the bore of a sample tube which is subjected to a very high heat, so that the sample, upon entering the tube, is atomized. The analyzing beam of the spectroscope is then directed through the bore of the sample tube and the atomized contents may then be quantitatively analyzed. In most instances, the sample tube is a graphite tube that is electrically heated to temperatures that range up to approximately 3,000° C. It is therefore apparent that the apparatus closely associated with the sample tube must be provided with adequate cooling facilities to prevent damage from the high heat.

Figure 1:
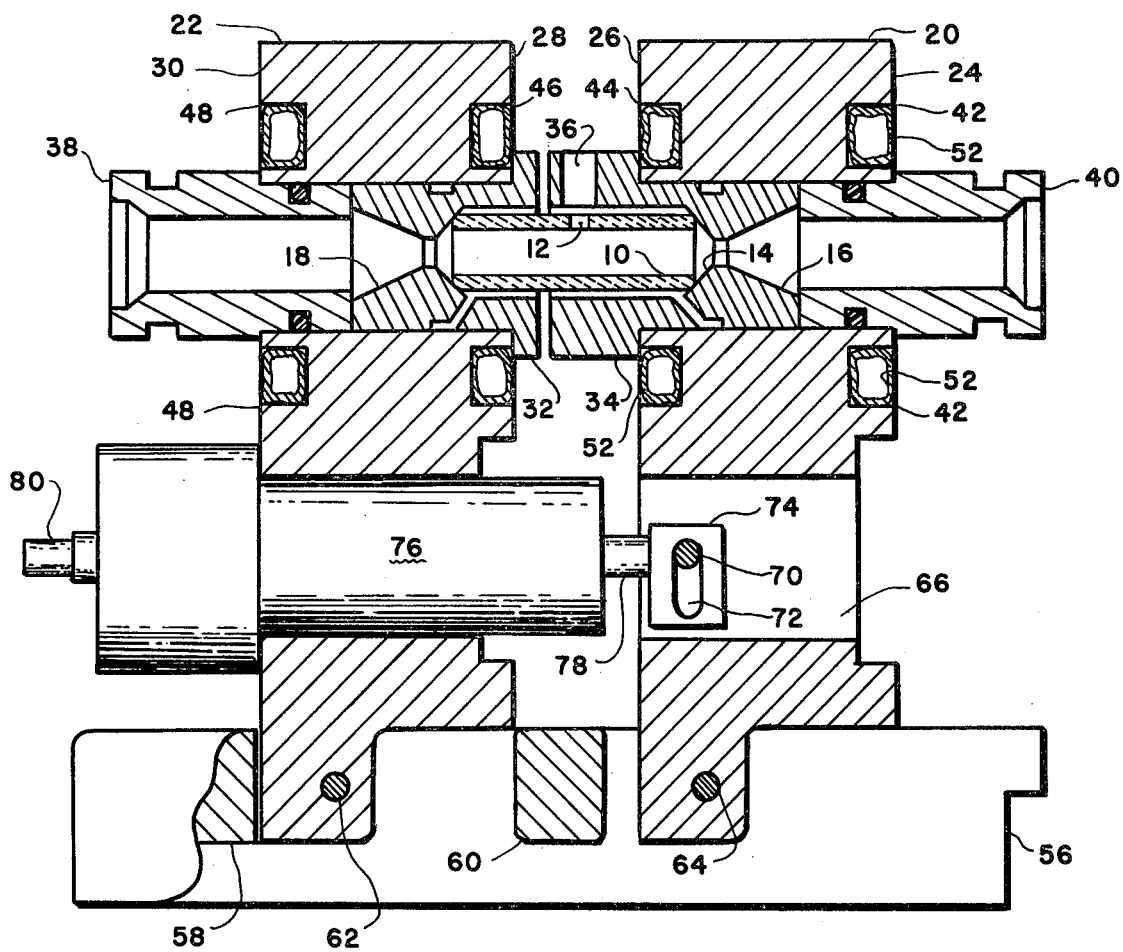
FIG. 1 is a sectional elevation view of the flameless atomization apparatus illustrating the cooling jacket housings and the means for pivotally separating the housings.

FIG. 1 is a sectional elevation view of the apparatus for supporting and heating a graphite sampler tube 10 provided with a radial sample inlet aperture 12 located near the center of the tube. The ends of graphite tube 10 are slightly tapered to provide a flat beveled surface that engages the conical internal surfaces 14 of electrodes 16 and 18 at the opposite ends of tube 10. Electrodes 16 and 18 are circular in cross-section and are fitted into corresponding apertures in cooling jacket housings 20 and 22, respectively. Housings 20 and 22 are preferably rectangular with parallel end faces 24 and 26 on housing 20 and parallel faces 28 and 30 on housing 22. Electrodes 16 and 18 are provided with flanged inner ends 32 and 34 and end faces 26 and 28 are normally separated from each other by the amount necessary to provide for the flanges 32 and 34. Flange 34 is wider than corresponding flange 32, since flange 34 must be provided with a sample admitting port 36 which is coaxial with the aperture 12 in the sample tube 10.

When electrical current is applied to the electrodes 16 and 18 and the sample tube 10 is heated to its elevated temperature, it is apparent that heat will be readily conducted from the tube 10 through the electrodes 16 and 18, the housings 20 and 22, and also to the tubular inserts 38 and 40 which may be provided to carry transparent windows (not shown). This excessive heat will obviously cause damage to the component parts of the apparatus unless adequately cooled. Therefore, housings 20 and 22 are provided with U-shaped cooling channels, such as the channels 42 in the end face 24, channel 44 in the end face 26, channel 46 in the end face 28, and channel 48 in the end face 30. Each of these channels is in close proximity with the respective housing apertures containing the electrodes 16 or 18.

Figure 2:
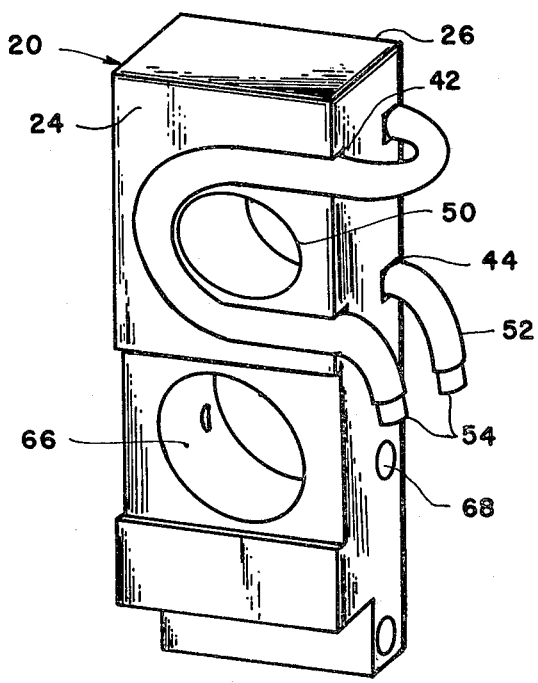
FIG. 2 is a perspective drawing illustrating the positioning of the coolant tubes within the cooling housing channels.

FIG. 2 is a perspective view of the cooling jacket housing 20 and illustrates the U-shaped channel 42 in the surface 24 and the channel 44 in the surface 26, each surrounding and coaxial with the aperture 50 which supports the electrode 16 and tubular insert 40 of FIG. 1. It will be noted from an examination of FIG. 1 that cooling jacket housings 20 and 22 are identical in order to simplify and therefore reduce the cost of manufacture.

As best illustrated in FIG. 2, the U-shaped channels 42 and 44 do not directly carry a coolant but support a seamless tubing 52 which is tightly pressed into the channels 42 and 44. Prior to its installation, tube 52 is preferably filled with a low melting point bismuth alloy, such as Wood's metal, and the tube is then firmly pressed into the channel to thereby insure good heat transfer. After installing the tube 52 first in the U-shaped channel on one surface, such as surface 24, and then bending the tube to engage the channel 44 in the second surface 26, the bismuth alloy is melted from the tube 52. Thereafter, when in operation, liquid coolant is supplied to and drawn off through connectors 54 in the tube 52.

As previously indicated, the housings 20 and 22 are identical and are mounted in a base unit in the channel between two parallel structures, such as the structure 56 of FIG. 1. The structures are interconnected by connecting block 58 at the end of the base unit adjacent housing 22 and by an intermediate connecting block 60, which is positioned to prevent the stationary housing 22 from moving about its pivot pin 62 which extends between the two parallel structures and through the bottom portion of the housing 22. The housing 20, which is identical with housing 22, is connected between the base structures, such as structure 56, by a pivot pin 64.

As shown in FIG. 2, each of the housings, such as the housing 20, contains a circular aperture 66, which extends completely through the housing. A hole 68 is drilled laterally through the center of the aperture 66 and, as illustrated in FIG. 1, supports a pin 70 within a slot 72 in a crosshead member 74. The aperture in housing 22 that corresponds to the aperture 66 in the housing 20, carries a reversible actuator 76 which is preferably pneumatic and contains a cylinder (not shown) that drives a piston rod 78 connected to the crosshead member 74. Air pressure applied to, or air withdrawn from the actuator 76 through its connector 80, will exert a force against pin 70 which will force the housing 20 to rotate about its pivot pin 64, as best illustrated in FIG. 3.

Figure 3:
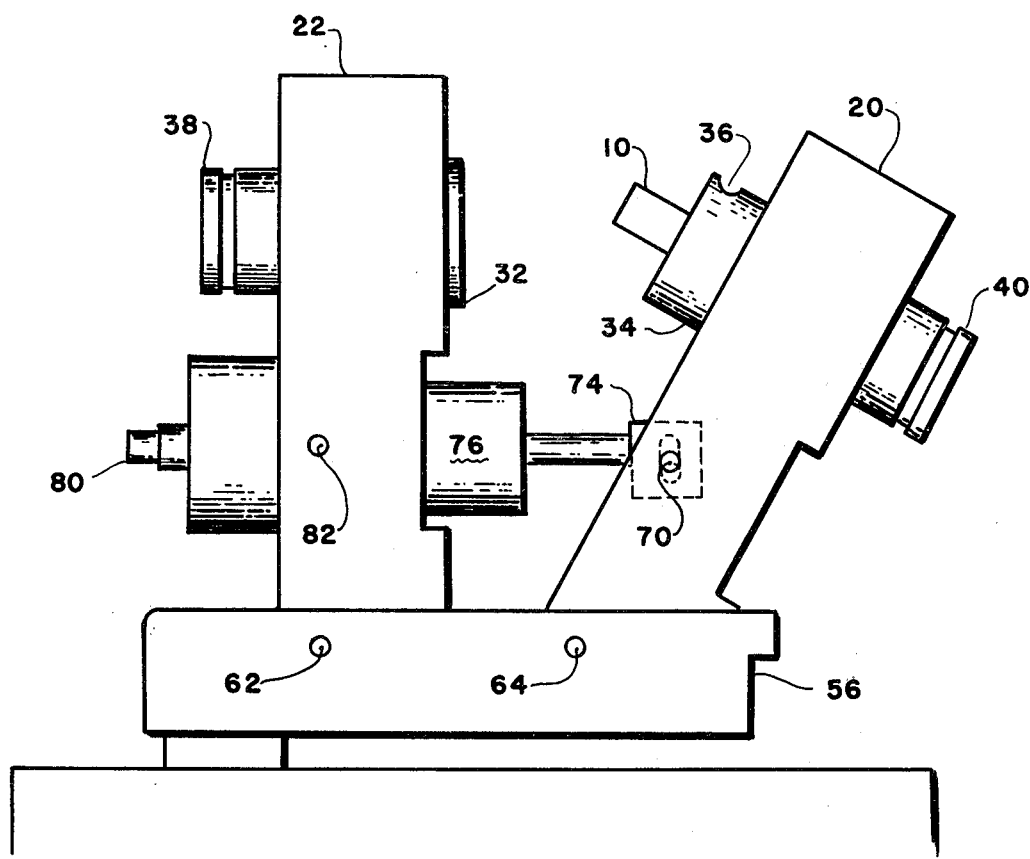
FIG. 3 is an elevation view of the apparatus illustrated in FIG. 1 showing the pivotal separation of the cooling jacket housings.

FIG. 3 is an elevation view showing housings 20 and 22 separated so that the graphite sample tube 10 may be readily removed from the electrode 34 and also to facilitate inspection of the bores or apertures in the electrodes 32 or 34. As shown in the figure, actuator 76, which is secured in the aperture of housing 22 by a pin 82, is extended so that its rod 78 and attached crosshead member 74 can exert a force against the pin 70 in housing 20 so that the housing 20 pivots about its pivot pin 64. Since the base of the housing 20 pivots in a channel between two base structures 56, it is free to move so that the bores of the electrodes 32 and 34 may readily be inspected for possible damage.

What is claimed is:

1. In a sample tube mounting structure for flameless atomic absorption spectroscopy, first and second electrode members for supporting the ends of a sample tube and for applying heating current therethrough, first and second cooling jacket housings having coaxial apertures, each for supporting one of the said electrodes, and power actuating means for separating said housings to enable the removal of said sample tube, the improvement comprising:
    at least one channel in each of the first and second cooling jacket housings, said channels being in close proximity to the respective electrode supporting aperture; and
    a seamless coolant tubing within each said channel in surface to surface heat transfer contact with the corresponding housing and adapted to carry a flow of cooling liquid to cool the corresponding housing and electrode member carried thereby.

2. The structure claimed in claim 1 wherein each of said housings has at least two parallel surfaces substantially perpendicular to the axis of the aperture in said housing, each of said two surfaces having a substantially U-shaped channel about the aperture and exposed through the corresponding surface, and wherein said coolant tubings are disposed within said U-shaped channels in said two surfaces respectively with each tubing extending about the corresponding aperture.

3. The structure claimed in claim 1 wherein said first coolant jacket housing is an elongated rectangular member having said electrode supporting aperture adjacent a first end and a pivot member adjacent its second end.

4. The structure claimed in claim 3 further including power actuator means coupled between said first and second ends of said first housing for pivotally moving said first end away from said second housing.

5. The structure claimed in claim 4 wherein said actuator is a pneumatic actuator.

6. The structure claimed in claim 4 wherein said first and second housings are substantially identical in structure and having coaxial apertures positioned between their first and second ends, the aperture in said second housing supporting said power actuator, the aperture in said first housing having a transverse pin engaging a slotted crosshead member attached to the piston rod of said power actuator.

7. The structure according to claim 2 wherein the tubing carried by each housing is continuous, each tubing including a portion extending from and end of the channel on one surface of the housing to an end of the channel on the other surface of the same housing.

8. A pair of electrode members for use in a flameless atomic absorption spectrometer, which includes first and second cooling jacket housings having coaxial apertures, each of said electrodes comprising a cylindrical outer surface and a radial flange at its inner end, each of said electrode members being mountable with its cylindrical outer surface disposed within the aperture of one of said housings so that its radial flange engages the inner radially extending surface of its housing to define a narrow slot between the radial flange of one electrode member and the radial flange of the other electrode member; the inner surface of each of said electrode members having a cylindrical portion adjacent its flange end, and a radially inwardly directed first conical portion extending from said cylindrical portion toward the outer end of the electrode member for holding one end of a graphite tube, and a radially outwardly flared second conical portion extending from the first conical portion towards the outer end of the electrode member.

9. A pair of electrode members according to claim 8 wherein the flange of one electrode member is substantially thicker than the flange of the other so that it extends beyond the middle of the graphite tube when the graphite tube is mounted between the first conical portions of the two electrodes, said thicker electrode member having a radial bore which is in alignment with a radial bore in the graphite tube when said graphite tube is mounted between the first conical portions of the two electrode members.

10. Apparatus according to claim 8 including at least one channel in each of the first and second cooling jacket housings, said channels being in close proximity to said electrode supporting apertures, and a seamless coolant tubing within each said channel in surface to surface heat transfer contact with the corresponding housing and adapted to flow cooling liquid to cool the corresponding housing and electrode member carried thereby.

11. Apparatus according to claim 10 wherein each of said housings has at least two parallel surfaces substantially perpendicular to the axis of the aperture in the corresponding housing, each of said two surfaces having a substantially U-shaped channel about the corresponding aperature and exposed through the corresponding surface, said cooling tubing being fitted into said U-shaped channels in each of said two surfaces and entending about said aperture.

* * * * *